US008858883B2

(12) United States Patent
Dowling et al.

(10) Patent No.: US 8,858,883 B2
(45) Date of Patent: Oct. 14, 2014

(54) METHOD AND SYSTEM FOR CAPTURE AND USE OF INTACT VESICLES ON ELECTRODEPOSITED HYDROPHOBICALLY MODIFIED BIOPOLYMER FILMS

(75) Inventors: Matthew Dowling, Washington, DC (US); Srinivasa R. Raghavan, Silver Spring, MD (US); Neeraja Dashaputre, College Park, MD (US); Douglas Stephen English, Derby, KS (US); Vishal Javvaji, Chantilly, VA (US); Gregory F. Payne, Hunt Valley, MD (US); Philip R. DeShong, Silver Spring, MD (US)

(73) Assignees: University of Maryland, College Park, College Park, MD (US); Wichita State University, Wichita, KS (US)

( * ) Notice: Subject to any disclaimer, the term of this patent is extended or adjusted under 35 U.S.C. 154(b) by 0 days.

(21) Appl. No.: 13/310,579

(22) Filed: Dec. 2, 2011

(65) Prior Publication Data

US 2012/0252703 A1 Oct. 4, 2012

Related U.S. Application Data (60) Provisional application No. 61/419,159, filed on Dec. 2, 2010.

(51) Int. Cl.
| | |
|---|---|
| *G01N 15/06* | (2006.01) |
| *G01N 33/00* | (2006.01) |
| *G01N 33/48* | (2006.01) |
| *A61L 15/44* | (2006.01) |
| *A61F 13/00* | (2006.01) |
| *G01N 33/543* | (2006.01) |
| *A61L 15/28* | (2006.01) |
| *G01N 33/548* | (2006.01) |

(52) U.S. Cl.
CPC ..... *A61F 13/00017* (2013.01); *A61L 2300/626* (2013.01); *A61L 15/44* (2013.01); *G01N 33/5438* (2013.01); *A61F 13/00063* (2013.01); *A61L 2300/104* (2013.01); *A61L 15/28* (2013.01); *A61L 2300/404* (2013.01); *A61L 2300/414* (2013.01); *G01N 33/548* (2013.01); *G01N 33/5436* (2013.01); *A61L 2300/406* (2013.01); *G01N 33/5432* (2013.01)
USPC ........... 422/68.1; 422/50; 422/82.01; 436/43; 436/63

(58) Field of Classification Search
USPC ...................................... 422/50, 68.1; 436/43
See application file for complete search history.

(56) References Cited

U.S. PATENT DOCUMENTS

| 4,532,134 A | 7/1985 | Malette et al. |
| 4,572,906 A | 2/1986 | Sparkes et al. |

(Continued)

OTHER PUBLICATIONS

Nikolelis et al., A Minisensor for the Rapid Screening of Sucralose Based on Surface-stabilized Bilayer Lipid Membranes, Biosensors & Bioelectronics 15:439-444 (2000).

(Continued)

*Primary Examiner* — Brian J Sines
(74) *Attorney, Agent, or Firm* — Whiteford, Taylor & Preston, LLP; Joseph L. Morales (57) ABSTRACT

A biosensor comprising an electrically conductive substrate coated with a modified chitosan biopolymer that has been electrodeposited on the substrate, wherein said modified chitosan biopolymer comprises at least one vesicle binding molecule. The biosensor is manufactured by a method where a modified chitosan biopolymer is electrodeposited on a substrate. The method is also used to manufacture a modified chitosan biopolymer film by electrodeposition of the chitosan on the substrate and later removing the film from the substrate after electrodeposition. The resulting film can be used in bandages to treat various types of wounds. The biosensor can also be used to detect various analytes in samples.

20 Claims, 9 Drawing Sheets

(56) References Cited

U.S. PATENT DOCUMENTS

| | | | |
|---|---|---|---|
| 4,752,466 A | 6/1988 | Saferstein et al. | |
| 4,895,724 A | 1/1990 | Cardinal et al. | |
| 5,243,094 A | 9/1993 | Borg | |
| 5,426,182 A | 6/1995 | Jenkins et al. | |
| 5,900,479 A | 5/1999 | Glasser et al. | |
| 5,919,574 A | 7/1999 | Hoagland | |
| 6,140,089 A | 10/2000 | Aebischer et al. | |
| 6,371,975 B2 | 4/2002 | Cruise et al. | |
| 6,458,147 B1 | 10/2002 | Cruise et al. | |
| 6,548,081 B2 | 4/2003 | Sadozai et al. | |
| 6,602,952 B1 | 8/2003 | Bentley et al. | |
| 6,663,653 B2 | 12/2003 | Akerfeldt | |
| 6,827,727 B2 | 12/2004 | Stalemark et al. | |
| 6,830,756 B2 | 12/2004 | Hnojewyj | |
| 6,864,245 B2 | 3/2005 | Vournakis et al. | |
| 6,890,344 B2 | 5/2005 | Levinson | |
| 6,899,889 B1 | 5/2005 | Hnojewyj et al. | |
| 6,949,114 B2 | 9/2005 | Milo et al. | |
| 6,958,325 B2 | 10/2005 | Domb | |
| 6,994,686 B2 | 2/2006 | Cruise et al. | |
| 6,995,137 B2 | 2/2006 | You et al. | |
| 7,247,314 B2 | 7/2007 | Hnojewyj et al. | |
| 7,279,001 B2 | 10/2007 | Addis et al. | |
| 7,288,532 B1 | 10/2007 | Payne et al. | |
| 7,318,933 B2 | 1/2008 | Hnojewyj | |
| 7,351,249 B2 | 4/2008 | Hnojewyj et al. | |
| 7,482,503 B2 | 1/2009 | Gregory et al. | |
| 7,820,872 B2 | 10/2010 | Gregory et al. | |
| 7,892,414 B1* | 2/2011 | Sumner | 205/778 |
| 2002/0028181 A1 | 3/2002 | Miller et al. | |
| 2002/0068151 A1 | 6/2002 | Kim et al. | |
| 2004/0001893 A1 | 1/2004 | Stupp | |
| 2005/0038369 A1 | 2/2005 | Gregory et al. | |
| 2005/0147656 A1 | 7/2005 | McCarthy | |
| 2005/0181027 A1 | 8/2005 | Messinger | |
| 2006/0094060 A1 | 5/2006 | Jarhede et al. | |
| 2006/0167116 A1 | 7/2006 | Uchegbu et al. | |
| 2006/0269485 A1 | 11/2006 | Friedman et al. | |
| 2007/0055364 A1 | 3/2007 | Hossainy | |
| 2007/0148215 A1 | 6/2007 | Teslenko et al. | |
| 2007/0172821 A1* | 7/2007 | Wu et al. | 435/6 |
| 2008/0029390 A1* | 2/2008 | Roche et al. | 204/403.06 |
| 2008/0103228 A1 | 5/2008 | Falcone et al. | |
| 2008/0254104 A1* | 10/2008 | Raghavan et al. | 424/445 |
| 2009/0062849 A1 | 3/2009 | Dowling | |
| 2009/0192429 A1 | 7/2009 | Daniels et al. | |
| 2009/0226391 A1 | 9/2009 | Roberts et al. | |
| 2011/0052665 A1 | 3/2011 | Hardy et al. | |
| 2011/0217785 A1* | 9/2011 | Liu et al. | 436/86 |
| 2012/0058970 A1 | 3/2012 | Dowling | |
| 2012/0252703 A1 | 10/2012 | Dowling | |

OTHER PUBLICATIONS

Paul S. Cremer and Steven G. Boxer, Formation and Spreading of Lipid Bilayers on Planar Glass Supports, J. Phys. Chem. B 103(13):2554-2559 (1999).
Puu et al., Retained Activities of Some Membrane Proteins in Stable Lipid Bilayers on a Solid Support, Biosensors and Bioelectronics 10:463-476 (1995).
Zhu et al., Reversible Vesicle Restraint in Response to Spatiotemporally Controlled Electrical Signals: A Bridge between Electrical and Chemical Signaling Modes, Langmuir 23(1)286-291 (2007).
Rodriguez, M.S., et al "Interaction between chitosan and oil under stomach and duodenal digestive chemical conditions" Biosci. Biotechnol. Biochem. 69 (11), 2057-2062 (2005).
Rongen et al., Liposomes and Immunoassays, J. Immunol. Methods 204:105-133 (1997).
Stavroula Sofou and James L. Thomas, Stable Adhesion of Phospholipid Vesicles to Modified Gold Surfaces, Biosensors and Bioelectronics 18:445-455 (2003).
Szymanska et al., Fullerene Modified Supported Lipid Membrane as Sensitive Element of Sensor for Odorants, Biosensors & Bioelectronics 16:911-915 (2001).
Tangpasuthadol, Surface Modification of Chitosan Films. Effects of Hydrophobicity on Protein Adsorption, Carbohydrate Res. 338:937-942 (2003).
Tanweer A. Khan and Kok Khiang Peh, A Preliminary Investigation of Chitosan Film as Dressing for Punch Biopsy Wound in Rats, J. Pharm. Pharmaceut. Sci. 6(1):20-26 (2003).
US Office Action, Application Publication No. 20080254104, Apr. 14, 2011.
US Office Action, Application Publication No. 20080254104, Nov. 8, 2010.
US Office Action, Application Publication No. 20090062849, Mar. 5, 2012.
US Office Action, Application Publication No. 20090062849, Sep. 21, 2012.
US Office Action, Application Publication No. 20120058970, Sep. 21, 2012.
US Office Action, Application Publication No. 20110280857, May 14, 2012.
US Office Action, Application Publication No. 20110280857, Jan. 28, 2013.
Whang, Hyun Suk et al., Hemostatic Agents Derived from Chitin and Chitosan, J. Macromolecular Science 45:309-323 (2005).
Wu et al., Spatially Selective Deposition of a Reactive Polysaccharide Layer onto a Patterned Template, Langmuir 19 (3):519-524 (2003).
Wu et al., Voltage-Dependent Assembly of the Polysaccharide Chitosan onto an Electrode Surface, Langmuir 18 (22):8620-8625 (2002).
Yoshina-Ishii et al.,Diffusive Dynamics of Vesicles Tethered to a Fluid Supported Bilayer by Single-Particle Tracking, Langmuir 22(13):5682-5689 (2006).
Yoshina-Ishii et al.,General Method for Modification of Liposomes for Encoded Assembly on Supported Bilayers, J. Am. Chem. Soc. 127(5):1356-1357 (2005).
Zhang, Jing. Drug Delivery: Self-Assembled Nanoparticles based on Hydrophobically Modified chitosan as Carriers for Doxorubicin, Nanomedicine, Elsevier. Aug. 2007. pp. 258-265.
Zhdanov et al. Adsorption and Spontaneous Rupture of Vesicles Composed of Two Types of Lipids (Langmuir 2006, 22, 3477-3480).
Zhdanov et al., Comments on Rupture of Adsorbed Vesicles (Langmuir 2001, 17, 3518-3521).
Zhu et al., Bioinspired Vesicle Restraint and Mobilization Using a Biopolymer Scaffold, Langmuir 22(7):2951-2955 (2006).
Desbrieres, J. et al. "Hydrophobic derivatives of chitosan: Characterization and rheological behaviour." International Journal of Biological Macromolecules. vol. 19. pp. 21-28. 1996.
Durian, Douglas J., et al. "Making a frothy shampoo or beer." Physics Today. pp. 62-63. May 2010.
Redepenning, J. et al. "Electrochemical preparation of chitosan/hydroxyapatite composite coatings on titanium substrates." Journal of Biomedical Materials Research. vol. 66A. pp. 411-416. 2003.
Alam, Hasan B., et al. Comparative Analysis of Hemostatic Agents in a Swine Model of Lethal Groin Injury, J. Trauma 54:1077-1082 (2003).
Allerbo et al., Simulation of lipid vesicle rupture induced by an adjacent supported lipid bilayer patch (Colloids and Surfaces B: Biointerfaces 2011, 82, 632-636).
Ankit R. Patel and Curtis W. Frank, Quantitative Analysis of Tethered Vesicle Assemblies by Quartz Crystal Microbalance with Dissipation Monitoring: Binding Dynamics and Bound Water Content, Langmuir 22(18):7587-7599 (2006).
Boukobza et al., Immobilization in Surface-Tethered Lipid Vesicles as a New Tool for Single Biomolecule Spectroscopy, J. Phys. Chem. B 105(48):12165-12170 (2001).
Brandenberg, Greg et al. Chitosan: A New Tropical Hemostatic Agent for Diffuse Capillary Bleeding in Brain Tissue, Neurosurgery 15(1): 9-13 (1984).
Burkatovskaya, Marina et al., Use of Chitosan Bandage to Prevent Fatal Infections Developing From Highly Contaminated Wounds in Mice, Biomaterials 27:4157-4164 (2006).

(56) References Cited

OTHER PUBLICATIONS

Chenite, A. et al "Rheological characterization of thermogelling chitosan/glycerol-phosphate solutions" Carbohydrate Polymers 46, 39-47 (2001).

Chiaki Yoshina-Ishii and Steven G. Boxer, Arrays of Mobile Tethered Vesicles on Supported Lipid Bilayers, J. Am. Chem. Soc. 125(13):3696-3697 (2003).

Cooper et al., A Vesicle Capture Sensor Chip for Kinetic Analysis of Interactions with Membrane-Bound Receptors, Anal. Biochem. 277:196-205 (2000).

Coster, Bag-On-Valve Series Offers Faster Filling and Better Drop Resistance. 2007. Downloaded from the world wide web on Jan. 18, 2012 <http://www.coster.com/news/eng/2007-10-18_AE_bov/AE_Manchester_BOV_eng.pdf.>.

Anderluh et al., Properties of Nonfused Liposomes Immobilized on an L1 Biacore Chip and Their Permeabilization by a Eukaryotic Pore-forming Toxin, Anal. Biochem. 344:43-52 (2005).

D. D. Lasic and D. Papahadjopoulos, Liposomes Revisited, Science 267(5202):1275-1276 (1995).

Dan D. Lasic, Novel Applications of Liposomes, Trens in Biotechnology (TIBTECH) 16:307-321 (1998).

Kotze, Awie F., et al. "Comparison of the effect of different chitosan salts and N-trimethyl chitosan chloride on the permeability of intestinal epithelial cells (Caco-2)." Journal of Controlled Release. vol. 51. pp. 35-46. 1998.

Dimitrievski et al., Influence of Lipid-Bilayer-Associated Molecules on Lipid-Vesicle Adsorption (Langmuir 2010, 26 (8), 5706-5714).

Dimitrievski et al., Simujlations of Lipid Vesicle Adsorption for Different Lipid mixtures (Langmuir 2008, 24, 4077-4091).

Eldin, Mohy et al. Chitosan Modified Membranes for Wound Dressing Applications: Preparations, Characterization and Bio-Evaluation. Trend Biomater. Atif.Organs. vol. 22 (3). pp. 158-168.

Esquenet et al.,Structural and Rheological Properties of Hydrophobically Modified Polysaccharide Associative Networks, Langmuir 20(9):3583-3592 (2004).

Fernandes et al., Electrochemically Induced Deposition of a Polysaccharide Hydrogel onto a Patterned Surface, Langmuir 19(10):4058-4062 (2003).

Fu et al., Protein stability in controlled-release systems, Nature Biotechnology 18:24-25 (2000).

GlaxoSmithKline. Bactroban Ointment: Prescribing Information. Research Triangle Park, NC, May 2005. Downloaded from the world wide web on Jan. 17, 2013 <https://www.gsksource.com/gskprm/htdocs/documents/BACTROAN-OINTMENTS.PDF>.

Gregory F. Payne and Srinivasa R. Raghavan, Chitosan: a Soft Interconnect for Hierarchical Assembly of Nano-scale Components, Soft Matter 3:521-527 (2007).

Hirano and Noishiki, The Blood Compatibility of Chitosan and N-Acylchitosans, J. Biochem. Materials Res. 413-417 (1985).

Hong et al., Two-step Membrane Binding by Equinatoxin II, a Pore-forming Toxin from the Sea Anemone, Involves an Exposed Aromatic Cluster and a Flexible Helix, J. Biol. Chem. 277(44):41916-41924 (2002).

Hook et al., Supported Lipid Bilayers, Tethered Lipid Vesicles, and Vesicle Fusion Investigated Using Gravimetric, Plasmonic, and Microscopy Techniques, Biointerphases 3(2) (Jun. 2008).

Hou, et al. "Preparation and characterization of RGD-immobilized chitosan scaffolds," Biomaterials 26 (2005) 3197-3206, published Oct. 14, 2004.

Jung et al., Quantification of Tight Binding to Surface-Immobilized Phospholipid Vesicles Using Surface Plasmon Resonance: Binding Constant of Phospholipase A2, J. Am. Chem. Soc. 122(17):4177-4184 (2000).

Kaler et al., Phase Behavior and Structures of Mixtures of Anionic and Catlonlc Surfactants, J. Phys. Chem. 96(16): 6698-6707 (1992).

Kaler et al., Spontaneous Vesicle Formation in Aqueous Mixtures of Single-Tailed Surfactants, Science 245(4924): 1371-1374 (1989).

Khan et al., Mechanical, Bioadhesive Strength and Biological Evaluations of Chitosan Films for Wound Dressing, J. Pharm. Pharmaceut. Sci. 3(3):303-311 (2000).

Kheirabadi, Bijan S. et al., Hemostatic Efficacy of Two Advanced Dressings in an Aortic Hemorrhage Model in Swine, J. Trauma Injury, Infection, and Critical Care, 59:25-35 (2005).

Kjoniksen et al., Light Scattering Study of Semidilute Aqueous Systems of Chitosan and Hydrophobically Modified Chitosans, Macromolecules 31(23):8142-8148 (1998).

Koehler et al., Microstructure and Dynamics of Wormlike Micellar Solutions Formed by Mixing Cationic and Anionic Surfactants, J. Phys. Chem. B 104(47):11035-11044 (2000).

Kozen, Buddy G. et al., An Alternative Hemostatic Dressing: Comparison of CELOX, HemCon, and QuikClot, Acad. Emerg. Med. 15:74-81(2008).

Kubota, et al. Gelation Dynamics and Gel Structure Fibrinogen, Colloids Surf. B. Biointerfaces 38:103-109 (2004).

Lee et al., Transition from Unilamellar to Bilamellar Vesicles Induced by an Amphiphilic Biopolymer, Phys. Review Letters, 96:048102-1-048102-4 (2006).

Lee et al., Vesicle-Biopolymer Gels: Networks of Surfactant Vesicles Connected by Associating Biopolymers, Langmuir 21(1):26-33 (2005).*

Li et al., Multivesicular Liposomes for Oral Delivery of Recombinant Human Epidermal Growth Factor, Arch Pharm Res 28(8):988-994 (2005).*

Lu, S. et al. "Preparation of Water-Soluble Chitosan" Journal of Applied Polymer Science 91, 3497-2503 (2004).*

Lunelli et al., Covalently Anchored Lipid Structures on Amine-Enriched Polystyrene, Langmuir 21(18):8338-8343 (2005).*

Malette, William G. et al. Chitosan: A New Hemostatic, The Annals of Thoracic Surgery 36(1):55-58 (1983).*

Mansur Yalpani and Laurence D. Hall, Some Chemical and Analytical Aspects of Polysaccharide Modifications. Formation of Branched-Chain, Soluble Chitosan Derivatives, Macromolecules 17(3):272-281 (1984).*

Mathivet et al., Shape Change and Physical Properties of Giant Phospholipid Vesicles Prepared in the Presence of an AC Electric Field, Biophysical Journal 70:1112-1121 (1996).*

Meier, Wolfgang et al., Vesicle and Cell Networks: Interconnecting Cells by Synthetic Polymers, Langmuir 12:5028-5032 (1996).*

Michael I. Fisher and Torbjorn Tjarnhage, Structure and Activity of Lipid Membrane Biosensor Surfaces Studied with Atomic Force Microscopy and a Resonant Mirror, Biosensors & Bioelectronics 15:463-471 (2000).*

Naumann et al., Proton Transport Through a Peptide-tethered Pilayer Lipid Membrane by the H+-ATP Synthase from Chloroplasts Measured by Impedance Spectroscopy, Biosensors and Bioelectronics 17:25-34 (2002).*

New ! Pioneer Chip L1 Improved binding studies in model membrane systems, BIA Journal No. 2 1998.*

* cited by examiner

METHOD AND SYSTEM FOR CAPTURE AND USE OF INTACT VESICLES ON ELECTRODEPOSITED HYDROPHOBICALLY MODIFIED BIOPOLYMER FILMS

CROSS REFERENCE TO RELATED APPLICATION

The present application claims priority under 35 U.S.C. §119 to U.S. Provisional Application Ser. No. 61/419,159 filed on Dec. 2, 2010, which is incorporated herein by reference in its entirety.

STATEMENT OF GOVERNMENT RIGHTS

This invention was made with government support under CBET0650650 awarded by the National Science Foundation. The government has certain rights in the invention

FIELD OF THE INVENTION

The present invention generally relates to the field of biopolymeric films. In particular, this invention relates to a method for the preparation of modified biopolymeric films by electrodeposition onto a substrate, devices incorporating the modified biopolymeric films, use of such devices for capture of vesicles and membranes, and lastly the use of the modified films with functionalized vesicles captured on the film.

BACKGROUND OF THE INVENTION

Vesicles (or liposomes) are self-assembled "nano-containers" formed by lipids or surfactants in aqueous solution.[1] These structures are ~100 nm in size and comprise an aqueous core and a lipid bilayer. The aqueous core can be used to encapsulate hydrophilic molecules such as drugs, proteins, or genes, while hydrophobic and amphiphilic substances can be integrated into vesicle bilayers.[1] Few, if any, other nanostructures demonstrate this level of versatility as carriers of useful payloads. Accordingly, vesicles have been explored and exploited for a myriad of applications, including targeted drug delivery, gene transfection, imaging agents, biosensors, food science, and cosmetics.[2]

Recently, there has been considerable interest into the capture of intact vesicles at precise locations on solid substrates.[3-14] The motivation for such studies includes: (a) fundamental aspects, e.g., related to vesicles as biological models for adherent cells; as well as (b) applied aspects related to the fabrication of biosensors or modified biomaterials. For example, the internal volume of intact vesicles would be available for entrapping biomolecules, drugs, or fluorescent molecules, which could be useful for sensor and immunoassay applications. In addition, proteins embedded in vesicle bilayers are expected to more closely mimic their in vivo function compared to the same proteins in supported planar bilayers.[4,12] There is particular interest in creating "vesicle arrays" via the spatially controlled immobilization of vesicles, which could spawn a new generation of biomolecular assay tools.[4,9]

Previous attempts to capture intact vesicles with spatial precision have employed DNA tethering,[4-6] covalent binding to gold or polystyrene,[7,8] or biotin-streptavidin linking schemes.[10-12] These methods generally involve labor-intensive experimental procedures or expensive chemical labels. An alternate simpler approach is to use amphiphilic polymers bearing hydrophobic (lipophilic) moieties as tethers to bind either supported lipid bilayers or vesicles to surfaces.[13-18] This approach has been used to capture label-free vesicles on the commercially available Biacore L1 chip;[13,14] however, this approach does not offer significant spatial resolution. A greater level of spatial and temporal control over vesicle capture (i.e., onto specific areas of a given surface at a given time) could be advantageous for many applications, including for the creation of vesicle arrays.

SUMMARY OF THE INVENTION

Disclosed is a biosensor, comprising an electrically conductive substrate coated with a modified chitosan biopolymer that has been electrodeposited on the substrate, wherein said modified chitosan biopolymer comprises at least one vesicle binding molecule. A preferred embodiment of the invention comprises a method of manufacturing a biosensor, comprising electrodepositing a modified chitosan biopolymer on a substrate by applying voltage to the substrate, wherein the biopolymer is capable of coating the substrate upon application of electricity and wherein the modified chitosan biopolymer comprises at least one vesicle binding molecule.

Further disclosed, is a bandage, comprising a modified chitosan biopolymer and a functionalized vesicle, wherein the film is manufactured by the steps of electrodeposition of the modified chitosan biopolymer on a substrate and removing the modified chitosan film from the substrate.

BRIEF DESCRIPTION OF THE DRAWINGS

The numerous advantages of the present invention may be better understood by those skilled in the art by reference to the accompanying figures in which:

FIG. 5 is a fluorescent pictures demonstrating the capture of vesicles & liposomes specific to electrodeposited films of hydrophobically modified chitosan (H) but not of unmodified variants (C). Top images: Green-filtered (shown in grey herein) fluorescence micrographs showing deposition of NHS-tagged hm-chitosan on the left electrode and NHS-tagged chitosan on the right electrode of a two-electrode chip. The chips are then incubated with vesicles for 10 min, followed by rinsing with DI water. Bottom images: Red-filtered fluorescence micrographs showing the presence of DiI-tagged vesicles on the electrodes. The results in (a) (left-column) are obtained with catanionic surfactant vesicles, while those in (b) (right-column) are obtained with liposomes. In both cases, the stronger signals from the left electrodes indicate that vesicles are anchored preferentially to the hm-chitosan film than to the chitosan one.

DETAILED DESCRIPTION OF THE INVENTION

The invention summarized above may be better understood by referring to the following description and claims, which should be read in conjunction with the accompanying drawings in which like reference numerals are used for like parts and steps. The following description is of a particular embodiment of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Method for Manufacturing a Modified Chitosan Biopolymer Film by Electrodeposition.

One aspect of a preferred embodiment of the present invention provides a method for preparation of a modified chitosan biopolymeric film (or matrix) that is electrodeposited on a substrate. Chitosan solidifies in a temporal and spatially selective manner on the substrate. In one such embodiment, various types of Chitosan may be utilized such as the following chitosan salts: chitosan chloride, chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine substituted chitosan and salts thereof. It is contemplated that any chitosan salt is capable of depositing on an electrode. While chitosan is a preferred biopolymer, it is contemplated that any biopolymer capable of solidifying on an electrode upon application of electricity to the electrode may be used in alternative embodiments of the present invention.

The substrate is a chip comprising one or more electrodes in one aspect of a preferred embodiment. Any material capable of conducting electricity may serve as an electrode, including but not limited to patterned gold, silver, copper, platinum, and palladium electrodes. Other electrodes include Indium Tin Oxide (ITO) coated glass, and Tin Dioxide ($SnO_2$) coated glass. A person of ordinary skill in the art, however, would recognize that any electrode capable of conducting electricity may be used in accordance with various preferred embodiments of the present invention. The electrodes can be arranged in any desired configuration on the chip. Various configurations of electrodes on the chip result in advantageous patterns of use of the modified polymers that are electrodeposited on the electrodes.

In a first step of the method, a substrate is prepared in order to deposit the film. In one preferred embodiment, the chip contains an electrode in no specific configuration. Alternatively, the chip may contain electrodes with various configurations. The configuration of the electrode results defined film pattern. Each electrode on the chip can be located at a specific address on the chip. As used herein, the term "address" refers to a specific location for an electrode on a chip. The capability of producing patterned films provides a special advantage over existing films. For example, in an application where the chip is used to identify two distinct analytes, each film at a specific address can be used to identify the presence of the analyte as explained in more detail below.

In a subsequent step, the substrate is placed in a solution containing the biopolymer. It is contemplated that in some preferred embodiments, the biopolymer solution consists of a hydrophobically modified polymer. Alternatively, the biopolymer solution may contain an unmodified biopolymer. In yet a further step of the process, electricity is applied to the substrate and the biopolymer solidifies on and around the substrate. If unmodified polymer was used, the resulting film coated substrate can be modified to include molecules capable of capturing vesicles or membranes on the film. In one preferred embodiment, the modifications are the addition of hydrophobic tails to the film as described in more detail below.

In a final step, the film is separated from the substrate. In an alternative embodiment, when an unmodified biopolymer is used, the separated unmodified film is further modified to include as described above to be able to interact with and capture vesicles and cells. It is contemplated that the film may be separated from the substrate by peeling it off mechanically. The separated film or the film coated substrate can be used for various applications as further described below.

Functionalization of the Modified Chitosan Film

In a further preferred embodiment, a method for preparing a functionalized chitosan film is provided. After the hydrophobically modified film is prepared, a further step comprises functionalizing the film through interaction of the biopolymer modifications with the membranes of vesicles (e.g., liposomes) or cells to capture the vesicle or cell. In one preferred embodiment, the vesicles may be empty "sacs" or may be functionalized via incorporation of bioactive agents or moieties either in the internal volume of the vesicle or as a part of membrane layer or in the vicinity. For example, the aqueous core of the vesicle can be filled with water-soluble drugs such as doxorubicin, nicardipine hydrochloride, methylsalicylic acid, and nitroglycerin. In other preferred embodiments, the bilayer can incorporate lipid-soluble drugs such as warfarin, pactlitaxel, diazepam, tamoxifen, progesterone, and estradial. In yet a further preferred embodiment, the vesicle can incorporate biological elements including, but not limited to, enzymes, antibodies, proteins, nucleic acids.

The vesicles may further be stimuli-responsive where, for example, the vesicles would deliver payload upon exposure to the stimuli, e.g., light, heat, pH, electricity, and other such triggers that allow the controlled release of functional contents of the vesicle. Some examples of such stimuli response vesicles, which are well-known in the art, include polyacrylic acid-block-6-[4-(4-cyanophenyl)phenoxyl]hexyl acrylate-co-6-[4-(4-methoxyphenylazo)phenoxyl]hexyl acrylate (P(BiPA-co-Azo)) copolymer vesicles (light), polyethylene oxide-block-poly(N-isopropylacrylamide) copolymer vesicles (heat), oleic acid vesicles (pH), and polystyrene-$\beta$-cyclodextrin/poly(ethylene oxide)-ferrocene supramolecular vesicles (electricity).

The size of these functional and stimuli responsive vesicles may range from 20 nm up to 20 μm in diameter. After the film is functionalized, it can be used for various applications either as a separated film or as part of the substrate. The functionalized film can be utilized in the methods described below.

In some alternative preferred embodiments, the polymeric film is modified by the addition of substrate specific moieties. In such alternative embodiments, for example, the modification is a ligand that a specific member receptor is capable of recognizing. The method of the present invention provides for the preparation of a patterned film in which some of the modifications are located in one particular location of the film, while other modifications are located in a different location. The resulting film is capable of capturing different vesicles and other molecules.

Method of Preparing a Biosensor.

In a preferred embodiment, a method for manufacturing a biosensor is provided. In one step of the method, a substrate is placed in a solution of modified chitosan polymer in solution. In a second step, the modified chitosan polymer is electrodeposited on the substrate by applying voltage to the substrate. The modified chitosan biopolymer the attaches to the substrate upon application of electricity to the substrate. The modified chitosan biopolymer comprises at least one vesicle binding molecule.

In one embodiment of the present invention a method for preparing a chip having at least two electrode addresses is described. Each electrode address on the chip comprises an electrically conductive substrate or electrode. Electricity can be independently applied to each electrode on the chip. The method provides a process for manufacturing a chip with different chitosan biopolymer films at different electrode addresses. In a first step of the method, the chip is prepared with at least two electrode addresses and each electrode address comprising an electrode that can be independently electrified. In a second step, the chip is placed in a solution containing a first type of biopolymer. Electricity is applied to a first electrode address and the film is allowed to form at the first electrode address.

In a subsequent step, the chip is placed in a second solution having a different type of chitosan biopolymer. Electricity is then applied to the second electrode address and the film is allowed to form at the second electrode address. If more than two electrode addresses are provided, it is contemplated that the process continues to proceed in the same sequence until all the electrode address in the chip are coated by different types of biopolymers. In an alternative embodiment, several chips may be coated with the same polymer while several others are coated with a different polymer. In yet a further alternative, some of the electrode addresses are coated and others are not coated at all. The biopolymers are modified to interact with different vesicles or cells. The coated chip may be used as provided or the various films on the chip may be separated from the electrodes for further use in various applications as described below.

Chitosan Biopolymer Based Biosensor

Figure 1A:
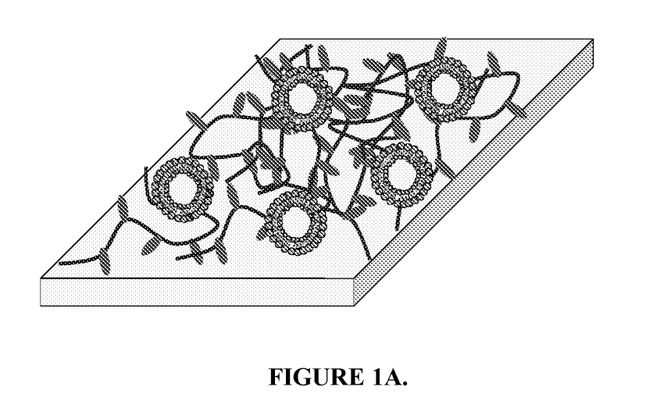
FIGS. 1a and 1b are a graphical representation of a biosensor in accordance with one aspect of a preferred embodiment.

One preferred embodiment of the present application is a modified chitosan biopolymer biosensor as shown in FIG. 1a comprising an electrically conductive substrate coated with a modified chitosan biopolymer that has been electrodeposited on the substrate, as described above. The modified chitosan biopolymer comprises a vesicle binding molecule. In a preferred embodiment, the biosensor further comprises a functionalized vesicle noncovalently bound to the vesicle binding molecule. As explained above, the vesicle binding molecule can be any molecule that is capable of noncovalently binding to a vesicle, by way of nonlimiting example, the vesicle binding molecule may be an alkyl, e.g., n-dodecyl substituent, functional group attached to the chitosan backbone. The electrically conductive substrate is an electrode as previously described to which the film attaches upon application of electricity. The electrode may be provided on a chip, where the chip is manufactured from silicon, copper oxide, germanium, gallium arsenide and graphene.

Figure 1B:
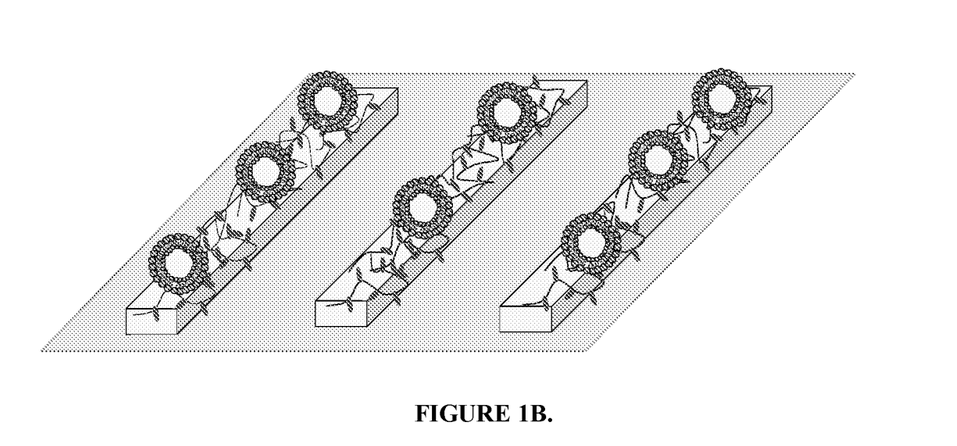
Figure 2A:
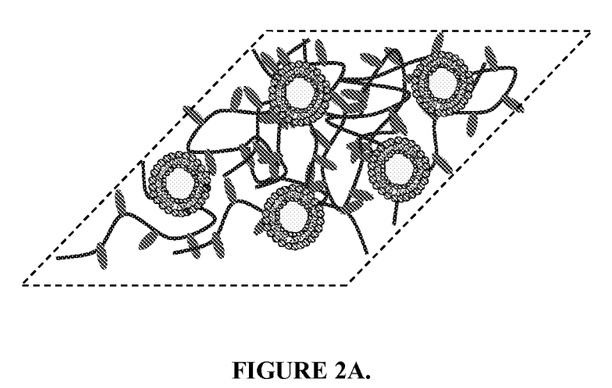
FIGS. 2a and 2b are a graphical representation of a biosensor in accordance with a further aspect of another preferred embodiment.
Figure 2B:
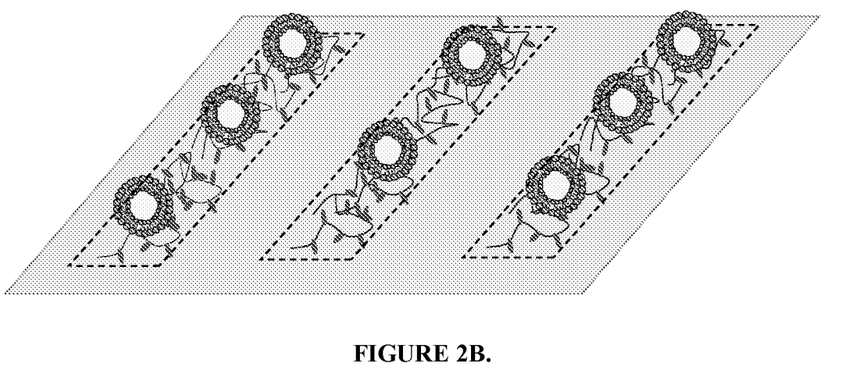
Figure 3:
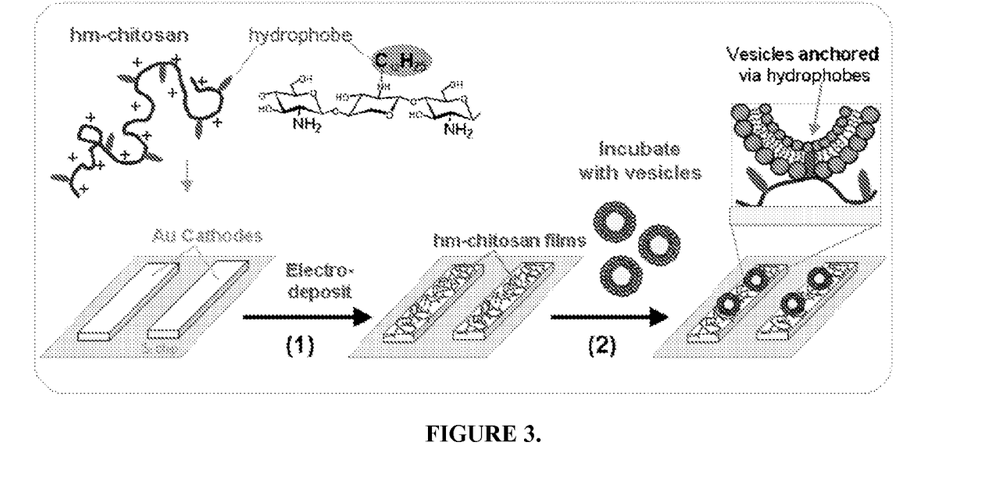
FIG. 3 is a graphical representation of the spatiotemporal capture of vesicles using hm-chitosan. The structure of hm-chitosan as well as a schematic of its chain are shown in the top left. The chain has a hydrophilic backbone shown in blue and pendant hydrophobes (C12 tails) that are shown in red. In step (1), thin films of hm-chitosan are electrodeposited onto gold cathodes that are patterned on a silicon chip. Next, in step (2), the chip is incubated with a solution of vesicles. Intact vesicles become spontaneously anchored onto the polymer films. The inset shows the likely mechanism for such anchoring, which is via non-covalent interaction between the hydrophobes on the polymer and vesicle bilayers.

In one preferred biosensor, the chip has a single electrode as shown in FIG. 1a. Alternatively, the chip may include multiple electrodes at various electrode addresses as sown in FIG. 1b. In one preferred embodiment, the electrodes are covered with the modified chitosan biopolymer. The chip is functionalized by attaching vesicles containing biological markers. In one embodiment of the present invention a first type of vesicle having a first type of biological marker is added to one electrode address. A second type of vesicle having a second type of biological marker is then added to a second electrode address. Ultimately, each address may have a different type of vesicle containing various biological markers. This type of biosensor is also referred to as a vesicle array. In one example, the biological markers may include biotin/streptavidin pairs, carbohydrate/lectin binding pairs, antibody/antigen pairs, oligosaccharide/lectin pairs, and complementary nucleic acid strands. The vesicle may include one member of the pair, which can be detected with the second member of the pair that has been labeled for the detection as understood by a person having ordinary skill in the art.

Alternatively, where each electrode address is coated with a different receptor for vesicles, the specific vesicles are targeted to each specific address. For example, one electrode address may be coated with a chitosan biopolymer having hydrophobic tails, e.g., n-dodecyl tails, will noncovalently attach to any type of vesicle or cell membrane. A second electrode address may be coated with a modified chitosan biopolymer with a tail that is a specific ligand for a receptor on a vesicle membrane.

Chitosan Biopolymer Based Biosensor Kit

Another embodiment of the present invention provides a chitosan biopolymer based biosensor kit. One preferred embodiment of the kit comprises a chip having a single electrode coated with a modified chitosan biopolymer film. The modified chitosan film comprises a hydrophobic substituent capable of noncovalently binding membranes and vesicles. The kit further comprises functionalized vesicles that can be attached to the chip for various biological tests as described above. The kit may further comprise other solutions and components for testing samples for the presence of specific analytes.

In an alternative embodiment, the kit comprises a chip having multiple electrodes at various electrode addresses coated with modified chitosan biopolymer films. The modified chitosan biopolymer comprises a hydrophobic substituent capable of noncovalently binding to the vesicles. In one example, the kit further comprises various functionalized vesicles comprising various biological markers. The vesicles can be deposited at different electrode addresses as arrays to conduct various biological tests. In a further embodiment, at least one of the electrode addresses is coated with a modified chitosan film with substituents that bind specifically to receptors in vesicle membranes. The kit, in such exemplary embodiment, comprises vesicles having the specific receptor that binds to the ligand on the modified chitosan. For example, vesicles may be prepared with biotinylated lipids. Such vesicles present biotin on their surface. These structures are able to capture streptavidin or streptavidin-associated moieties from the surrounding solution due to highly-specific binding between biotin and streptavidin. In a further example, vesicles can be prepared with amphiphilic glycoconjugates such as $C_8$-maltose, $C_8$-glucose, or $C_8$-maltotriose. The carbohydrate portion of the glycoconjugate is exposed on the surface of the vesicle. Such carbohydrates have strong binding affinities for specific types of lectins, e.g. concanavalin A and peanut aggluntinin, and can captures these molecules from the surrounding media.

Chitosan Biopolymer Based Bandages

In yet a further embodiment of the present invention provides a modified chitosan biopolymer film for treating wounds. The chitosan biopolymer film is prepared by the method described above and separated from the electrode. It is contemplated that the modified chitosan film in some preferred embodiments may include functionalized vesicles, which may deliver biologically active agents to wounds. The modified chitosan film may be combined with wound dressings to treat bleeding, burns, and other skin conditions requiring treatment.

In a further embodiment, the bandage can be provided as a kit. The kit has several components, including a modified chitosan polymer prepared in accordance with the method described above and separated from the electrodes. The kit further comprises functionalized vesicles that can be added to the modified chitosan film for treatment of wounds. The vesicle functionalized matrix can then be applied to a wound serving as a functional dressing. This dressing can provide protection from microbial invasion, acceleration of wound healing, improved hemostasis and prevention of fluid exudation.

The vesicles may incorporate payloads of anti-microbial agents (e.g. norfloxacin, silver, ampicillin and penicillin) for sterilization purposes and/or growth factors (e.g. platelet-derived growth factor (PDGF), epidermal growth factor (EGF), basic fibroblast growth factor (bFGF), and vascular endothelial growth factor (VEGF)) for accelerated healing purposes. These agents retain their bioactivity inside the vesicles and can be released in a sustained manner into the wound site as the vesicles degrade for sterilization and accelerated healing purposes, respectively. The biopolymer film itself improves hemostasis and prevents fluid exudation. Furthermore, the vesicles can have triggers as described above.

EXAMPLES

The following are some examples of preferred embodiments of the present invention.

Materials. Chitosan of medium molecular weight (190-310K) and Brookfield viscosity of 286 cps was obtained from Sigma-Aldrich. The reported degree of deacetylation was about 80%. Chitosan is soluble only under acidic conditions (pH<6.5) and here it was dissolved in 0.2 M acetic acid. The phospholipids L-α-phosphatidylcholine (PC) and biotinylated phosphatidylethanolamine (PE-biot), and the fluorescent lipid 1'-dioctadecyl-3,3,3',3'-tetramethylindocarbocyanine perchlorate (DiI) were purchased from Avanti Polar Lipids. The surfactants cetyltrimethylammonium tosylate (CTAT), sodium dodecyl benzenesulfonate (SDBS), and Triton X-100, the dye 5,6-carboxyfluorescein (CF), and the reagent n-dodecyl aldehyde were purchased from Sigma-Aldrich. Streptavidin bound to fluorescein isothiocyanate (FITC-streptavidin) and the succinimidyl ester of CF (NHS-fluorescein) were purchased from Fluka. All experiments were performed using distilled-deionized (DI) water.

Synthesis of Chitosan Derivatives. The hm-chitosan was synthesized by attaching n-dodecyl tails to the chitosan backbone via reaction with n-dodecyl aldehyde. The procedure has been reported in our earlier paper[23] and follows that described in the literature.[28-30] The degree of hydrophobic substitution follows the reaction stoichiometry and in this study it was fixed at ca. 2.5 mol % of the available amine groups. Fluorescently-labeled chitosan and hm-chitosan were synthesized by reacting the polymers with NHS-fluorescein, as previously reported in the literature.[20]

Vesicle and Liposome Preparation. Both surfactant vesicles and lipid vesicles (liposomes) have been used in this study. Catanionic surfactant vesicles[31,32] were prepared by mixing 0.7 wt % of the cationic surfactant CTAT and 0.3 wt % of anionic surfactant SDBS (~2:1 molar ratio) in DI water and gently stirring overnight. Dye-filled catanionic vesicles were prepared by combining 1 mM of CF with the CTAT/SDBS mixture, followed by separation of vesicles from free dye using a Sephadex G-50 column (from Roche). Liposomes were prepared by an extrusion method, as recommended by the manufacturer (Avanti Polar Lipids). Briefly, dried films of the lipids were hydrated under moderate stirring, freeze-thawed 5 times, and then passed through two double-stacked polycarbonate membrane filters (100 nm pores) using a Lipex pressurized extrusion system. Dye-filled liposomes were prepared in DI water from PC (20 mM) and CF (15 mM) and purified of free CF using the Sephadex G-50 column. Fluorescently labeled liposomes were prepared in DI water by combining the lipid PC (13 mM) with trace amounts (13 µM) of the fluorescent lipid DiI. For the streptavidin binding assay, biotinylated liposomes were prepared by combining PC and PE-Biotin in a molar ratio of 9:1, with a total lipid concentration of 1 wt %. Vesicle sizes in all cases were measured using a Photocor-FC dynamic light scattering (DLS) instrument.

Preparation of Giant Unilamellar Vesicles (GUVs). The GUVs were prepared by electroformation, as described in the literature.[33,34] The lipids (1 mg/mL) and DiI (7.7 µg/ml) were dissolved in chloroform. One drop of this solution (5 µL) was deposited onto the conducting side of an indium tin-oxide (ITO)-coated glass slide. The solvent was removed first under desiccation for 1 h, and then freeze-drying for 3 h. A chamber was then made by creating an O-ring out of Seal-Ease and then pressing a second ITO-coated slide, conducting side facing downward, above the original slide (gap depth of 1 mm). The chamber was hydrated with a solution of 100 mM sucrose in DI water via injection needle through the Seal-Ease; after injection, the needle was removed and the hole closed by Seal-Ease. Alligator clips were connected to both glass slides as well as a function generator (BK Precision 10 MHz Sweep/Function Generator 4017) via a BNC connector. An electric potential of AC 1.5 V at 10 Hz (corresponding electric field of 1500 V/m) was applied for 2 h at 55° C.; the frequency was then dropped to 1 Hz for an additional 50 min. In the process, GUVs were found to appear in the fluid in the chamber.

Figure 4:
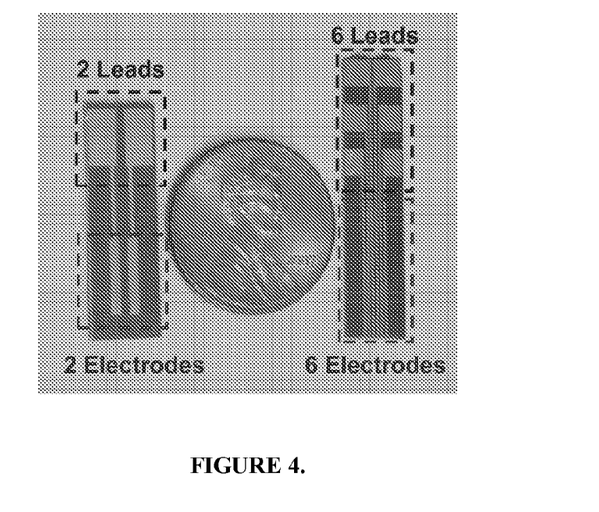
FIG. 4 is a photograph that shows exemplary substrates (micropatterned chips) in accordance with one embodiment of the present invention. The leads and electrodes are formed by depositing gold on a silicon wafer using lithographic techniques. On the left is a 2-electrode chip and on the right a 6-electrode chip. A US penny is shown for size comparison.

Electrodeposition. Electrodeposition was performed on "chips" fabricated from silicon wafers with deposited micropatterns of gold (FIG. 4). Fabrication procedures have been described in detail in our earlier papers.[19-21] Electrodeposition was performed by negatively biasing a specific lead on the chip while it was partially immersed in an aqueous solution containing 1 wt % of either chitosan or hm-chitosan at a pH~5. A DC power supply (model 6641C, Agilent Technologies) was used to supply a constant current to the chip and counter electrode over a 2 min period. Photomicrographs of fluorescent electrodeposited materials were taken by a fluorescence stereomicroscope (MZFLIII, Leica) equipped with a digital camera (Spot 32, Diagnostic Instruments). To observe CF or FITC fluorescence, the microscope was set with an excitation wavelength of 480 nm (bandwidth of 40 nm) and a long-pass emission filter at 510 nm. To observe DiI fluorescence, the filters were chosen with an excitation wavelength of 560 nm (bandwidth of 40 nm), and an emission filter of 610 nm. In all cases, Image J1.34S software from NIH was used to analyze images and quantify fluorescence intensity.

Cryo-TEM. C-FLAT holey carbon grids with a hole size of 1.2 mm were purchased from Electron Microscopy Sciences. Grids bearing hm-chitosan and surfactant vesicles were plunged into liquid ethane (−183° C.) using a Gatan CryoPlunge3, so as to form vitrified specimens and thereby preserve any molecular assemblies present. The samples were thereafter imaged on a JEOL-2100 LaB6 TEM at liquid nitrogen temperature.

Results.

Figure 5:
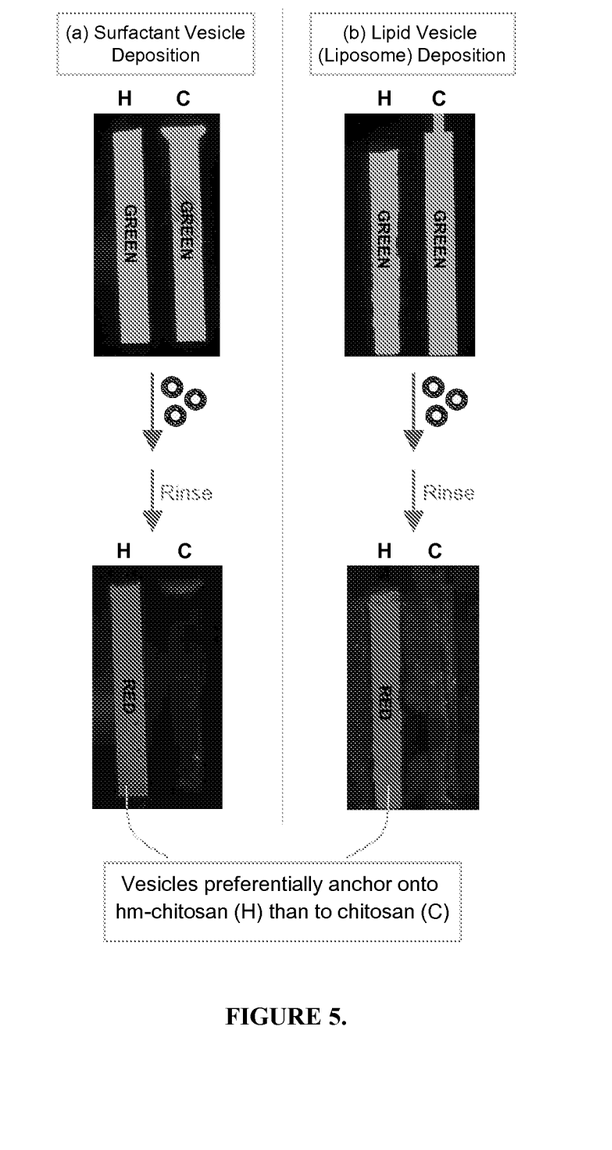

Vesicle Capture on hm-chitosan Films. A two-electrode chip as shown in FIG. 4 was prepared. We conducted sequential electrodeposition of hm-chitosan and chitosan (both tagged with the green fluorescent dye, NHS-fluorescein) on the left and right electrodes, respectively. This was done as follows: first, the right electrode was connected to the power supply and the other unconnected while the chip was immersed in a solution of chitosan. The connections were then switched (only left electrode connected) and the chip was immersed in a solution of hm-chitosan. After deposition, the electrodes were disconnected from the power supply, and the chips were rinsed several times with DI water. Both chitosan and hm-chitosan were shown to deposit on each electrode (FIG. 5 (top)) the two fluorescence images indicate successful deposition of both hm-chitosan and chitosan on the chip.

Next we examined the relative capabilities of hm-chitosan and chitosan to capture vesicles from solution. These experiments were conducted with both surfactant vesicles as well as lipid vesicles (liposomes). The catanionic surfactant vesicles (70/30 CTAT/SDBS, total 1 wt %) had an average diameter around 120 nm, as measured by DLS. The liposomes of PC were made by extrusion through 100 nm membrane filters and had an average diameter around 110 nm from DLS. Both the vesicles and the liposomes were tagged with the fluorescent lipid DiI, which incorporates into the bilayer membranes of the above structures. Note that DiI exhibits a red fluorescence, i.e., a distinct color compared to the green signal from the chitosan and hm-chitosan. We incubated the chip on the left with surfactant vesicles and the one on the right with the liposomes, both for 10 min. The chips were then rinsed three times with DI water to remove weakly adsorbed structures and then imaged under the fluorescence microscope using red filters. The resulting images (FIG. 5, bottom) show a significantly higher fluorescent signal from the hm-chitosan side compared to the chitosan-side—for both the surfactant vesicles and the liposomes. These results show that hm-chitosan is considerably more effective at capturing vesicles than chitosan.

Figure 6:
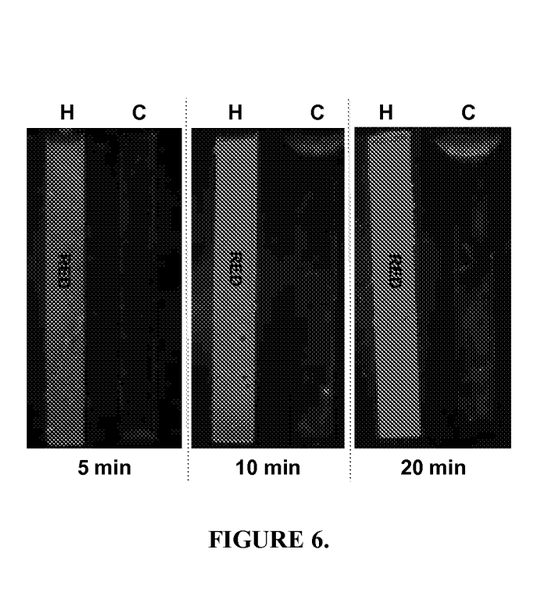
FIG. 6 is a picture that shows the effect of variation in the extent of vesicle capture based on the time of chip incubation with a vesicle solution. Hm-chitosan (H) and chitosan (C) are deposited on the left and right electrodes, respectively. The chip is incubated with a solution of surfactant vesicles for different lengths of time and then imaged by fluorescence microscopy. The images are red-filtered fluorescence micrographs showing DiI-tagged vesicles on the electrodes. A constant exposure time of 20 s at the excitation wavelength was used to obtain each image. The results show increasing capture of vesicles on the H side (increasing signal intensity) and negligible capture on the C side.

The superior effectiveness of hm-chitosan in capturing vesicles is a robust result and this is further proven by experiments with varying vesicle incubation times. For these experiments, surfactant vesicles were used and the time of chip incubation in the vesicle solution was varied from 5 to 10 to 20 min. All other experimental variables, including rinsing times and image exposure time were kept constant. The results in FIG. 6 show an increase in red fluorescence from the hm-chitosan electrode with increasing incubation time—the increase is quite significant between 5 and 10 min and slight between 10 and 20 min. In all cases, the signal from the hm-chitosan side dwarfs that from the chitosan side. Similar results were obtained for macroscopic films of chitosan and hm-chitosan simply dried onto glass slides and incubated with tagged surfactant vesicles for various time intervals.

Figure 7:
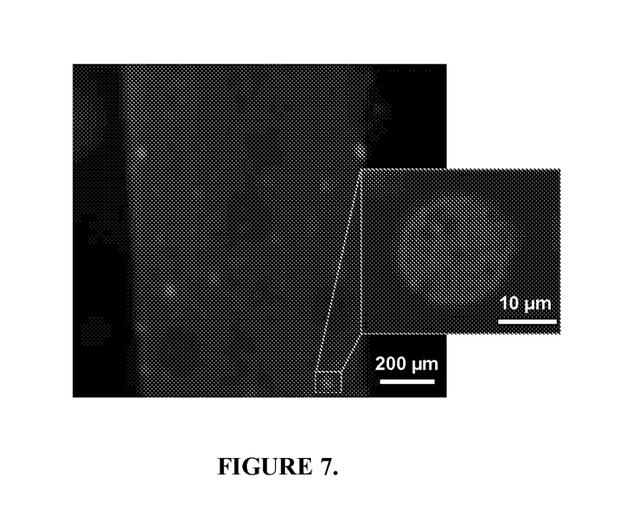
FIG. 7 is a picture showing immobilization of giant unilamellar vesicles (GUVs) on an hm-chitosan film. After 10 min incubation with DiI-tagged GUVs, multiple red-fluorescent 'hot spots' appear on the electrode bearing hm-chitosan. A zoomed-in image of a 'hot-spot' shows an intact GUV of ca. 20 μm diameter.

Intactness of Captured Vesicles. Next we show that the vesicles are intact in FIG. 5. In this case, we prepared a solution of fluorescently tagged giant unilamellar vesicles (GUVs) of phospholipids. Optical microscopy revealed that the GUVs ranged in size from 10 to 50 mm, which is typical of GUVs made via electroformation. We then incubated a chip bearing hm-chitosan in the GUV solution for 10 min, rinsed the chip and observed it under a fluorescence microscope. Note the fluorescent "hot spots" on the hm-chitosan film—these are shown at two different levels of magnification in FIGS. 7. Thus, large microsized GUVs were shown to remain intact when immobilized on an hm-chitosan film.

Figure 8:
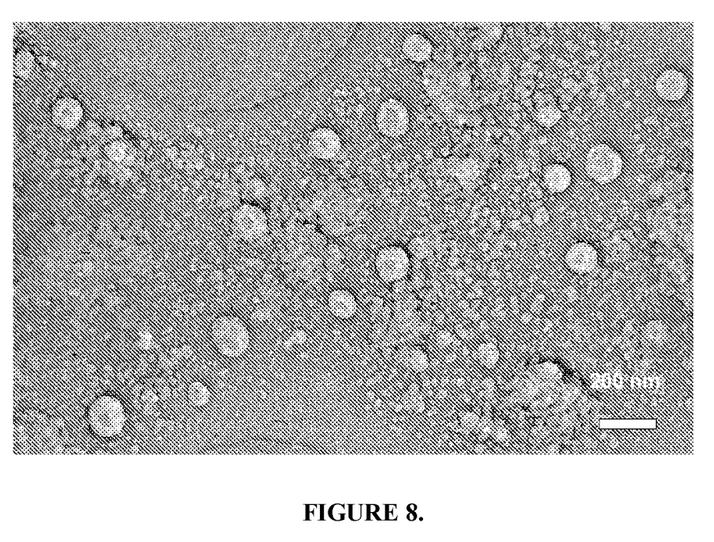
FIG. 8 is a cryo-transmission electron micrograph of vesicles captured on such films. Cryo-TEM image of vesicles on an hm-chitosan film. The hm-chitosan was deposited on the TEM grid and then used to capture surfactant vesicles from solution. The image shows numerous spherical objects of ~100-150 nm diameter, which are presumably intact vesicles.

Next, evidence for the intact capture of nanosized surfactant vesicles is provided by cryo-TEM. For these experiments, we deposited hm-chitosan directly on holey-carbon TEM grids. These grids were then incubated with surfactant vesicles, followed by a rinsing step with DI water to remove weakly adsorbed vesicles. The rinsed grids were maintained in an aqueous environment at room temperature. These grids were then prepared in the usual way for cryo-TEM (see Experimental Section) by plunging into liquid ethane. Observation of the vitrified specimens showed the presence of numerous spherical structures of 100-150 nm diameter (FIG. 8). These are evidently the surfactant vesicles and they all seem whole—no breaks or holes can be found on the vesicle shells. Thus, once again, the vesicles appear to have been captured intact.

Figure 9:
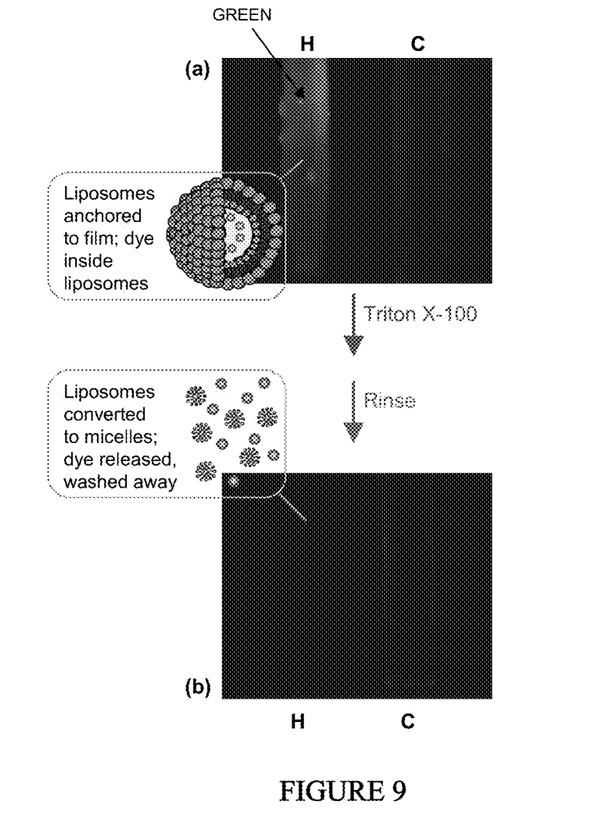
FIG. 9 is a scheme of experiment that demonstrates the release of contents from vesicles upon intentional rupture of previously intact vesicles. Evidence for capture of intact liposomes on hm-chitosan films. (a) Green-filtered fluorescence image showing preferential binding of liposomes (filled with the hydrophilic dye CF) to the hm-chitosan (H) side relative to the chitosan (C) side. The chip is then exposed to the detergent Triton X-100 and rinsed. The detergent disrupts the liposomes into micelles, as shown by the schematics, and the encapsulated dye is thus released and washed away. (b) Fluorescence image of the rinsed chip shows nearly complete loss of fluorescent signal, confirming disruption of originally intact liposomes.

Lastly, we present indirect functional evidence for the intactness of captured vesicles. In this experiment, we prepared liposomes containing the hydrophilic dye CF. We ensured that the dye was present only inside liposomal cores; free (unencapsulated) dye was removed via size-exclusion chromatography, as described in the Experimental Section. The biopolymers were left untagged for this experiment to avoid overlap with the green fluorescence from the CF. Again, hm-chitosan was deposited on the left electrode and chitosan on the right. The chip was then incubated with the CF-filled liposomes followed by rinsing with DI water. At this stage, FIG. 9a shows a strong green signal only on the hm-chitosan side, implying that the liposomes preferentially attached there. The only alternate explanation is that the fluorescence comes from free CF dye stuck to the hm-chitosan, i.e., that the liposomes had already been disrupted. To rule out this possibility, we added the detergent Triton X-100 into the solution above the chip. This detergent is known for its ability to disrupt liposomes into mixed micelles, whereupon dye in the liposomal cores would be released into solution (this is illustrated by the schematics in FIG. 9). After detergent addition and subsequent rinsing, FIG. 9b shows that the green signal has vanished from the hm-chitosan film. The loss of signal after detergent treatment necessarily implies that the liposomes were initially intact on the hm-chitosan surface in FIG. 9a.

Figure 10:
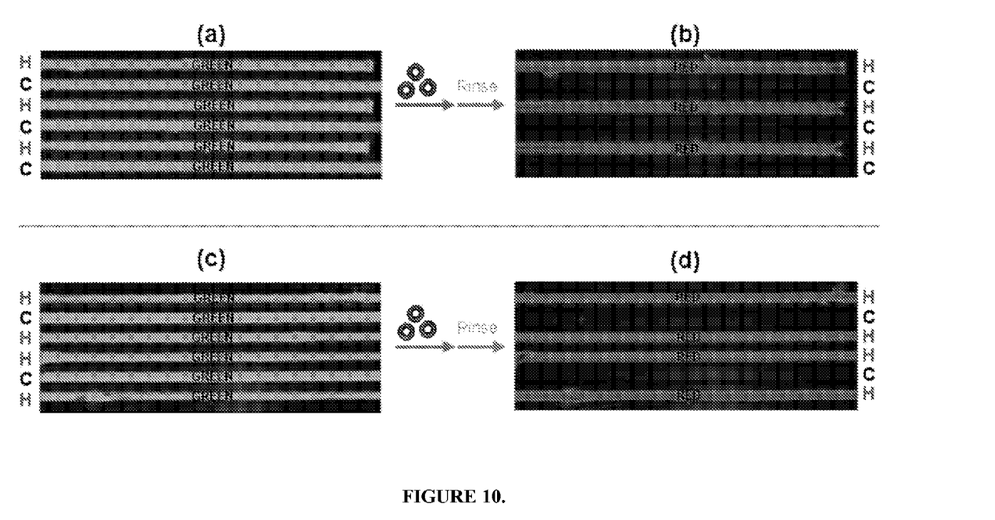
FIG. 10 is a picture demonstrating the capture of vesicles as a patterned substrate in accordance with one embodiment of the present invention. Patterning of vesicles on 6-electrode chips. (a) NHS-tagged hm-chitosan (H) and chitosan (C) are electrodeposited in an alternating pattern, HCHCHC. (b) Following contact with DiI-tagged surfactant vesicles and rinsing, the red fluorescence indicative of vesicles is found only on the H electrodes. (c) H and C are electrodeposited in an 'outside-inside' pattern, HCHHCH. (d) Once again, DiI-tagged surfactant vesicles are found anchored only on the H electrodes.

Spatial Control of Vesicle Capture. We now demonstrate the capability to create specific microscale patterns of vesicles on the chip. Towards this end, we used two 6-electrode chips with a view towards engineering two specific patterns of vesicles. On one chip we deposited hm-chitosan (H) and unmodified chitosan (C) in an alternating pattern, i.e., HCHCHC, on the 6 electrodes (FIG. 10a). After incubating the film with a solution of DiI-tagged surfactant vesicles, the signal indicative of vesicles is observed only on the hm-chitosan (H) electrodes (FIG. 10b). Next, on the other chip, we deposited the polymers in an 'outside-inside' pattern, i.e., HCHHCH (FIG. 10c). Incubation of the chip with the same tagged vesicles again results in a red signal only on the hm-chitosan (H) electrodes (FIG. 10d). Thus, in both cases, predetermined patterns of vesicles were successfully created. Such patterning can be easily extended to more complex designs and with finer resolution. Previous work with chitosan has indicated the resolution limits of electrodeposition to be on the order of 1 □m.[20] We view this work as a step towards the construction of "vesicle arrays" that could prove to be a useful tool for probing the properties of biomolecules such as membrane proteins.

Figure 11:
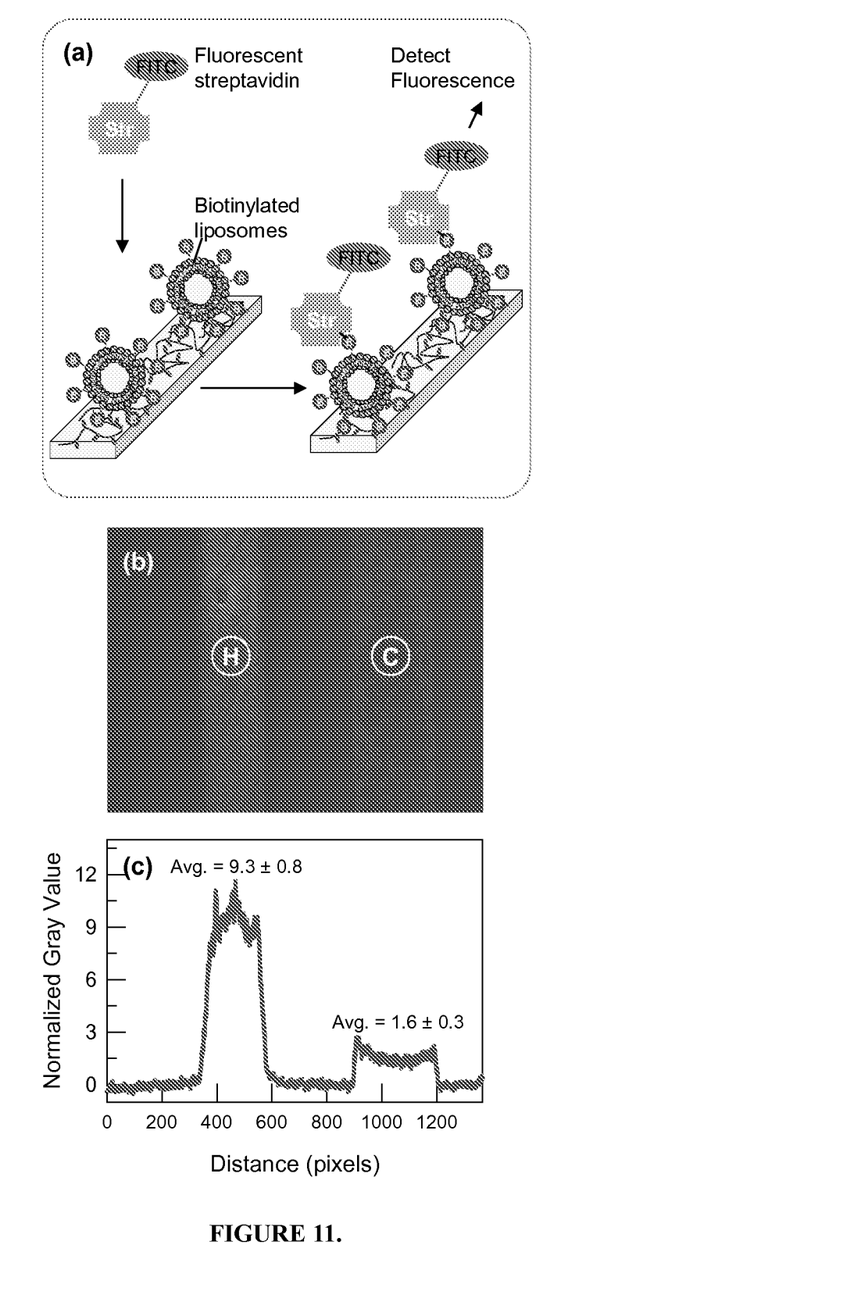
FIG. 11 is a scheme and result demonstrating the functionality of captured vesicles as a biosensing platform. Protein sensing via vesicles anchored to an hm-chitosan film. (a) Schematic of the experiment: biotin-decorated liposomes are first immobilized, then the chip is contacted with the fluorescently labeled protein, FITC-streptavidin. The binding of the protein is then detected by fluorescence microscopy. (b) Fluorescence image showing a strong signal from the hm-chitosan (H) electrode compared to the chitosan (C) electrode. The strong signal is indicative of protein binding to the biotins on the anchored liposomes. (c) Analysis of the intensities in (b). The average gray values for each electrode area are listed above the corresponding regions.

Use of captured vesicles as biosensor. Lastly, for immobilized vesicles to be useful in biosensing or binding assays, the vesicles should be able to access ligands from the external solution. To evaluate this aspect, we studied the interaction between surface-bound biotinylated liposomes and streptavidin in the surrounding solution. The experiment is depicted schematically in FIG. 11a. Biotinylated liposomes were prepared by combining PC and PE-biot in a molar ratio of 9:1. These liposomes were then contacted with a chip bearing hm-chitosan (H) and chitosan (C) films on adjacent electrodes. The chip was then rinsed with DI water and exposed to a solution containing fluorescently tagged streptavidin, a protein that non-covalently binds to biotin with extremely high affinity. Following a second rinsing, the results (FIG. 11b) show a significantly higher fluorescent signal from streptavidin on the hm-chitosan electrode than the chitosan electrode. The signals are quantified in the plot shown in FIG. 11c: the fluorescence is approximately 6 times higher on the hm-chitosan side (9.3±0.8 gray value) relative to the chitosan side (1.6±0.3 gray value). The high signal on the hm-chitosan side is evidently due to the binding of streptavidin to the biotinylated liposomes captured on that film. The binding of streptavidin to the chitosan side is not zero presumably because streptavidin (a negatively charged protein) can bind non-specifically to the positively charged chitosan, although most of these proteins are removed in the rinsing step.

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

References.

All references cited below and within the description above are incorporated herein by reference in their entirety.

[1] Lasic, D. D. "Novel applications of liposomes." *Trends. Biotechnol.* 1998, 16, 307-321.

[2] Lasic, D. D.; Papahadjopoulos, D. "Liposomes revisited." *Science* 1995, 267, 1275-1276.

[3] Christensen, S. M.; Stamou, D. "Surface-based lipid vesicle reactor systems: fabrication and applications." *Soft Matter* 2007, 3, 828-836.

[4] Yoshina-Ishii, C.; Boxer, S. G. "Arrays of mobile tethered vesicles on supported lipid bilayers." *J. Am. Chem. Soc.* 2003, 125, 3696-3697.

[5] Yoshina-Ishii, C.; Chan, Y. H. M.; Johnson, J. M.; Kung, L. A.; Lenz, P.; Boxer, S. G. "Diffusive dynamics of vesicles tethered to a fluid supported bilayer by single-particle tracking" *Langmuir* 2006, 22, 5682-5689.

[6] Hook, F.; Stengel, G.; Dahlin, A. B.; Gunnarsson, A.; Jonsson, M. P.; Jonsson, P.; Reimhult, E.; Simonsson, L.; Svedhem, S. "Supported lipid bilayers, tethered lipid vesicles, and vesicle fusion investigated using gravimetric, plasmonic, and microscopy techniques." *Biointerphases* 2008, 3, FA108-FA116.

[7] Lunelli, L.; Pasquardini, L.; Pederzolli, C.; Vanzetti, L.; Anderle, M. "Covalently anchored lipid structures on amine-enriched polystyrene." *Langmuir* 2005, 21, 8338-8343.

[8] Sofou, S.; Thomas, J. L. "Stable adhesion of phospholipid vesicles to modified gold surfaces." *Biosens. Bioelectr.* 2003, 18, 445-455.

[9] Jung, H.; Kim, J.; Park, J.; Lee, S.; Lee, H.; Kuboi, R.; Kawai, T. "Atomic force microscopy observation of highly arrayed phospholipid bilayer vesicle on a gold surface." *J. Biosci. Bioeng.* 2006, 102, 28-33.

[10] Jung, L. S.; Shumaker-Parry, J. S.; Campbell, C. T.; Yee, S. S.; Gelb, M. H. "Quantification of tight binding to surface-immobilized phospholipid vesicles using surface plasmon resonance: Binding constant of phospholipase A(2)." *J. Am. Chem. Soc.* 2000, 122, 4177-4184.

[11] Boukobza, E.; Sonnenfeld, A.; Haran, G. "Immobilization in surface-tethered lipid vesicles as a new tool for single biomolecule spectroscopy." *J. Phys. Chem. B* 2001, 105, 12165-12170.

[12] Patel, A. R.; Frank, C. W. "Quantitative analysis of tethered vesicle assemblies by quartz crystal microbalance with dissipation monitoring: Binding dynamics and bound water content." *Langmuir* 2006, 22, 7587-7599.

[13] Cooper, M. A.; Hansson, A.; Lofas, S.; Williams, D. H. "A vesicle capture sensor chip for kinetic analysis of interactions with membrane-bound receptors." *Anal. Biochem.* 2000, 277, 196-205.

[14] Anderluh, G.; Besenicar, M.; Kladnik, A.; Lakey, J. H.; Macek, P. "Properties of nonfused liposomes immobilized on an L1 Biacore chip and their permeabilization by a eukaryotic pore-forming toxin." *Anal. Biochem.* 2005, 344, 43-52.

[15] Knoll, W.; Frank, C. W.; Heibel, C.; Naumann, R.; Offenhausser, A.; Ruhe, J.; Schmidt, E. K.; Shen, W. W.; Sinner, A. "Functional tethered lipid bilayers." *J. Biotechnol.* 2000, 74, 137-58.

[16] Naumann, C. A.; Prucker, O.; Lehmann, T.; Ruhe, J.; Knoll, W.; Frank, C. W. "The polymer-supported phospholipid bilayer: Tethering as a new approach to substrate-membrane stabilization." *Biomacromolecules* 2002, 3, 27-35.

[17] Tanaka, M.; Sackmann, E. "Polymer-supported membranes as models of the cell surface." *Nature* 2005, 437, 656-663.

[18] Deng, Y.; Wang, Y.; Holtz, B.; Li, J. Y.; Traaseth, N.; Veglia, G.; Stottrup, B. J.; Elde, R.; Pei, D. Q.; Guo, A.; Zhu, X. Y. "Fluidic and air-stable supported lipid bilayer and cell-mimicking microarrays." *J. Am. Chem. Soc.* 2008, 130, 6267-6271.

[19] Wu, L. Q.; Gadre, A. P.; Yi, H. M.; Kastantin, M. J.; Rubloff, G. W.; Bentley, W. E.; Payne, G. F.; Ghodssi, R. "Voltage-dependent assembly of the polysaccharide chitosan onto an electrode surface." *Langmuir* 2002, 18, 8620-8625.

[20] Wu, L. Q.; Yi, H. M.; Li, S.; Rubloff, G. W.; Bentley, W. E.; Ghodssi, R.; Payne, G. F. "Spatially selective deposition of a reactive polysaccharide layer onto a patterned template." *Langmuir* 2003, 19, 519-524.

[21] Fernandes, R.; Wu, L. Q.; Chen, T. H.; Yi, H. M.; Rubloff, G. W.; Ghodssi, R.; Bentley, W. E.; Payne, G. F. "Electrochemically induced deposition of a polysaccharide hydrogel onto a patterned surface." *Langmuir* 2003, 19, 4058-4062.

[22] Payne, G. F.; Raghavan, S. R. "Chitosan: a soft interconnect for hierarchical assembly of nano-scale components." *Soft Matter* 2007, 3, 521-527.

[23] Lee, J. H.; Gustin, J. P.; Chen, T. H.; Payne, G. F.; Raghavan, S. R. "Vesicle-biopolymer gels: Networks of surfactant vesicles connected by associating biopolymers." *Langmuir* 2005, 21, 26-33.

[24] Lee, J. H.; Agarwal, V.; Bose, A.; Payne, G. F.; Raghavan, S. R. "Transition from unilamellar to bilamellar vesicles induced by an amphiphilic biopolymer." *Phys. Rev. Lett.* 2006, 96.

[25] Zhu, C.; Lee, J. H.; Raghavan, S. R.; Payne, G. F. "Bio-inspired vesicle restraint and mobilization using a biopolymer scaffold." *Langmuir* 2006, 22, 2951-2955.

[26] Zhu, C.; Wu, L. Q.; Wang, X.; Lee, J. H.; English, D. S.; Ghodssi, R.; Raghavan, S. R.; Payne, G. F. "Reversible vesicle restraint in response to spatiotemporally controlled electrical signals: A bridge between electrical and chemical signaling modes." *Langmuir* 2007, 23, 286-291.

[27] Li, H.; An, J. H.; Park, J. S.; Han, K. "Multivesicular liposomes for oral delivery of recombinant human epidermal growth factor." *Arch. Pharm. Res.* 2005, 28, 988-994.

[28] Desbrieres, J.; Martinez, C.; Rinaudo, M. "Hydrophobic derivatives of chitosan: Characterization and rheological behaviour." *Int. J. Biol. Macromol.* 1996, 19, 21-28.

[29] Kjoniksen, A. L.; Iversen, C.; Nystrom, B.; Nakken, T.; Palmgren, O. "Light scattering study of semidilute aqueous systems of chitosan and hydrophobically modified chitosans." *Macromolecules* 1998, 31, 8142-8148.

[30] Esquenet, C.; Terech, P.; Boue, F.; Buhler, E. "Structural and rheological properties of hydrophobically modified polysaccharide associative networks." *Langmuir* 2004, 20, 3583-3592.

[31] Kaler, E. W.; Murthy, A. K.; Rodriguez, B. E.; Zasadzinski, J. A. N. "Spontaneous Vesicle Formation in Aqueous Mixtures of Single-Tailed Surfactants." *Science* 1989, 245, 1371-1374.

[32] Kaler, E. W.; Herrington, K. L.; Murthy, A. K.; Zasadzinski, J. A. N. "Phase-Behavior and Structures of Mixtures of Anionic and Cationic Surfactants." *J. Phys. Chem.* 1992, 96, 6698-6707.

[33] Angelova, M. I.; Dimitrov, D. S. "Liposome electroformation." *Faraday Discuss.* 1986, 81, 303-306.

[34] Mathivet, L.; Cribier, S.; Devaux, P. F. "Shape change and physical properties of giant phospholipid vesicles prepared in the presence of an AC electric field." *Biophys. J.* 1996, 70, 1112-1121.

What is claimed is:

1. A biosensor, comprising:
   an electrically conductive substrate coated with a hyropbobically-modified chitosan biopolymer comprising at least one vesicle binding molecule; wherein the biopolymer has been electrodeposited on the substrate.

2. The biosensor of claim 1, wherein the modified chitosan electrodeposited on the substrate is selected from the group consisting of modified chitosan chloride, modified chitosan lactate, modified chitosan salicylate, modified chitosan pyrrolidone carboxylate, modified chitosan itaconate, modified chitosan niacinate, modified chitosan formate, modified chitosan acetate, modified chitosan gallate, modified chitosan glutamate, modified chitosan maleate, modified chitosan aspartate, modified chitosan glycolate and quaternary amine substituted chitosan and salts thereof.

3. The biosensor of claim 1, wherein the vesicle binding molecule is a hydrophobic molecule or a molecule that recognizes a specific receptor on the vesicle's membrane.

4. The biosensor of claim 1, wherein the substrate is an electrode.

5. The biosensor of claim 4, wherein the electrode is selected from the group consisting of gold, silver, copper, platinum, palladium, Indium Tin Oxide (ITO) coated glass, and Tin Dioxide ($SnO_2$) coated class electrodes.

6. The biosensor of claim 4, wherein the electrode is on a chip.

7. The biosensor of claim 5, wherein the chip is made of a material selected from the group consisting of silicon, copper oxide, germanium, gallium arsenide and grapheme.

8. The biosensor of claim 1, further comprising at least one vesicle.

9. The biosensor of claim 7, wherein the vesicle comprises a biological marker.

10. The biosensor of claim 9, wherein the biological marker is selected from the group consisting of biotin, streptavidin, oligosaccharides, fluorescent markers.

11. The biosensor of claim 1, wherein the substrate further comprises at least two electrode addresses.

12. The biosensor of claim 11, wherein at least one of said at least two electrode addresses is coated with a first modified chitosan biopolymer that is different from a second modified chitosan biopolymer that coats another of said at least two electrode addresses.

13. The biosensor of claim 11, wherein said first modified chitosan binds a first type of vesicle, while said second modified chitosan biopolymer binds a second type of vesicle.

14. A method of manufacturing a biosensor, comprising:
electrodepositing a hydrphobically-modified chitosan biopolymer on a substrate by applying voltage to the substrate, wherein the biopolymer is capable of coating the substrate upon application of electricity and wherein the modified chitosan biopolymer comprises at least one vesicle binding molecule.

15. The method of claim 14, wherein prior to said electrodepositing step the substrate is placed in a solution of the modified chitosan polymer.

16. The method of claim 15, wherein the chitosan is a modified chitosan salt selected from the group consisting of modified chitosan chloride, modified chitosan lactate, modified chitosan salicylate, modified chitosan pyrrolidone carboxylate, modified chitosan itaconate, modified chitosan niacinate, modified chitosan formate, modified chitosan acetate, modified chitosan gallate, modified chitosan glutamate, modified chitosan maleate, modified chitosan aspartate, modified chitosan glycolate and quaternary amine substituted modified chitosan and salts thereof.

17. The method of claim 14, further comprising the step of attaching at least one vesicle to the biopolymer.

18. The method of claim 14, wherein the substrate comprises at least two electrode addresses.

19. The method of claim 18, further comprising the step placing the substrate in a solution containing a first type of modified chitosan biopolymer and applying voltage to a first set of electrode addresses in order to coat the first set of electrode addresses with the first type of modified chitosan biopolymer.

20. The method of claim 19, further comprising the step placing the substrate in a solution containing a second type of modified chitosan biopolymer and applying voltage to a second set of electrode addresses in order to coat the second set of electrode addresses with the second type of modified chitosan biopolymer.

* * * * *